United States Patent [19]
Brandt et al.

[11] Patent Number: 5,104,543

[45] Date of Patent: Apr. 14, 1992

[54] PREPARATIVE CHROMATOGRAPHIC METHOD OF SEPARATION FOR PREPARING ENANTIOMERICALLY PURE HETRAZEPINES

[75] Inventors: Klaus Brandt; Jurgen Nagel, both of Ingelheim am Rhein, Fed. Rep. of Germany

[73] Assignee: Boehringer Ingelheim GmbH, Ingelheim am Rhein, Fed. Rep. of Germany

[21] Appl. No.: 678,504

[22] Filed: Apr. 1, 1991

[30] Foreign Application Priority Data

Apr. 2, 1990 [DE] Fed. Rep. of Germany ....... 4010528

[51] Int. Cl.$^5$ ........................................... B01D 15/08
[52] U.S. Cl. .................................. 210/635; 210/656; 540/560
[58] Field of Search ................ 540/560; 210/635, 656, 210/198.2

[56] References Cited

U.S. PATENT DOCUMENTS

| | | | |
|---|---|---|---|
| 4,094,984 | 6/1978 | Weber | 540/560 |
| 4,900,729 | 2/1990 | Stransky | 540/560 |
| 4,910,194 | 3/1990 | Moriwaki | 540/560 |
| 4,914,096 | 4/1990 | Houlihan | 540/560 |
| 4,937,240 | 6/1990 | Moriwaki | 540/524 |
| 4,968,794 | 11/1990 | Weber | 540/560 |
| 5,028,603 | 7/1991 | Tahara | 540/560 |

FOREIGN PATENT DOCUMENTS 254245  1/1988  European Pat. Off. ......... 210/198.2

*Primary Examiner*—Ernest G. Therkorn
*Attorney, Agent, or Firm*—Daniel Reitenbach; David Frankhouser; Mary-Ellen Timbers

[57] ABSTRACT

The invention relates to a method of separation by liquid chromatography for preparing enantiomerically pure hetrazines, using cellulose triacetate as a stationary phase and a polar solvent as a mobile phase.

4 Claims, 3 Drawing Sheets

PREPARATIVE CHROMATOGRAPHIC METHOD OF SEPARATION FOR PREPARING ENANTIOMERICALLY PURE HETRAZEPINES

The invention to a preparative chromatographic method of separation for preparing enantiomerically pure hetrazepines.

Substituted hetrazepines of general formula

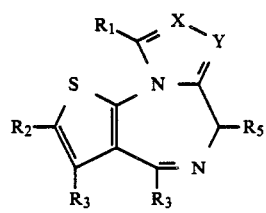

are known from the prior art as pharmaceutical compositions having a PAF-antagonistic activity, e.g. from European Patent Applications EP-A-0.176.927, EP-A-0.176.928, EP-A-0.176.929, EP-A-0.194.416, EP-A-0.230.942, EP-A-0.240.899, EP-A-0.254.245, EP-A-0.255.028, EP-A-0.268.242, EP-A-0.279.681, EP-A-0.284.359, EP-A-0.291.594, EP-A-0.298.466, EP-A-0.315.698, EP-A-0.342.456, EP-A-0.338.992, EP-A-0.328.924, EP-A-0.342.587, EP-A-0.338.993, the contents of which are hereby referred to.

Compounds of the above-mentioned structural type may contain an optically active carbon atom, depending on the definition of the substituents $R_2$, $R_3$ or $R_5$. Generally, such compounds are obtained as racemates when synthesised (starting from optically inactive starting compounds). It is known that the two enantiomers do not have the same pharmacological effects and it is therefore in the interests of modern drug research to use only the enantiomer which has the stronger pharmacological activity.

The aim is therefore to propose a process which can be carried out on an industrial scale for preparing enantiomerically pure hetrazepines of the structural type referred to hereinbefore.

DESCRIPTION OF THE PREFERRED EMBODIMENTS

Figure 1:
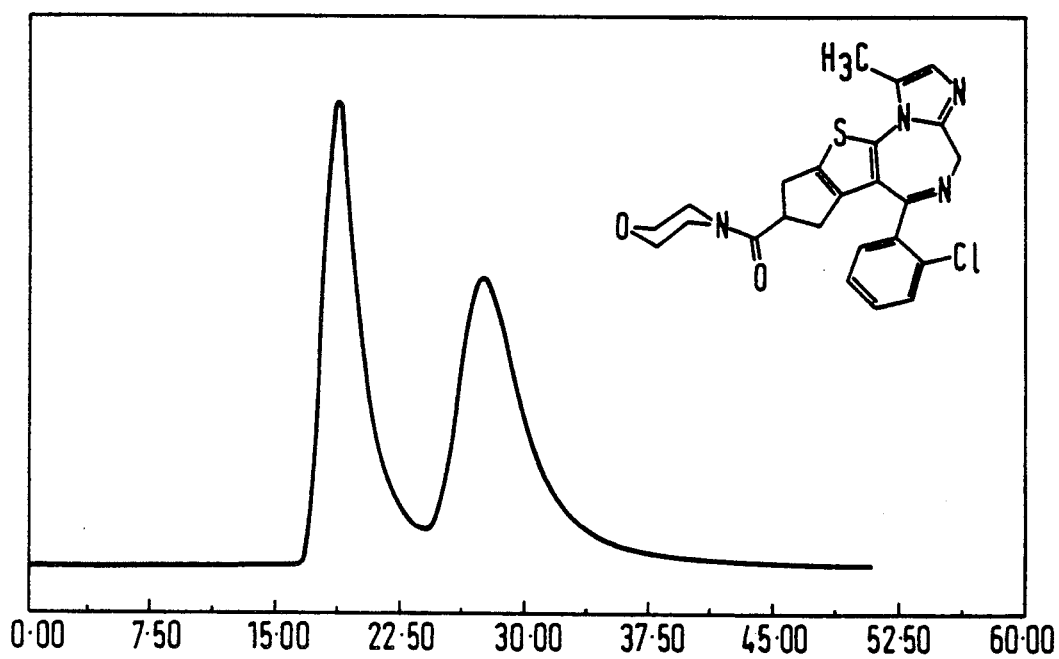
FIGS. 1, 2, 3, 4, and 5 each shows a different chromtogram.
Figure 2:
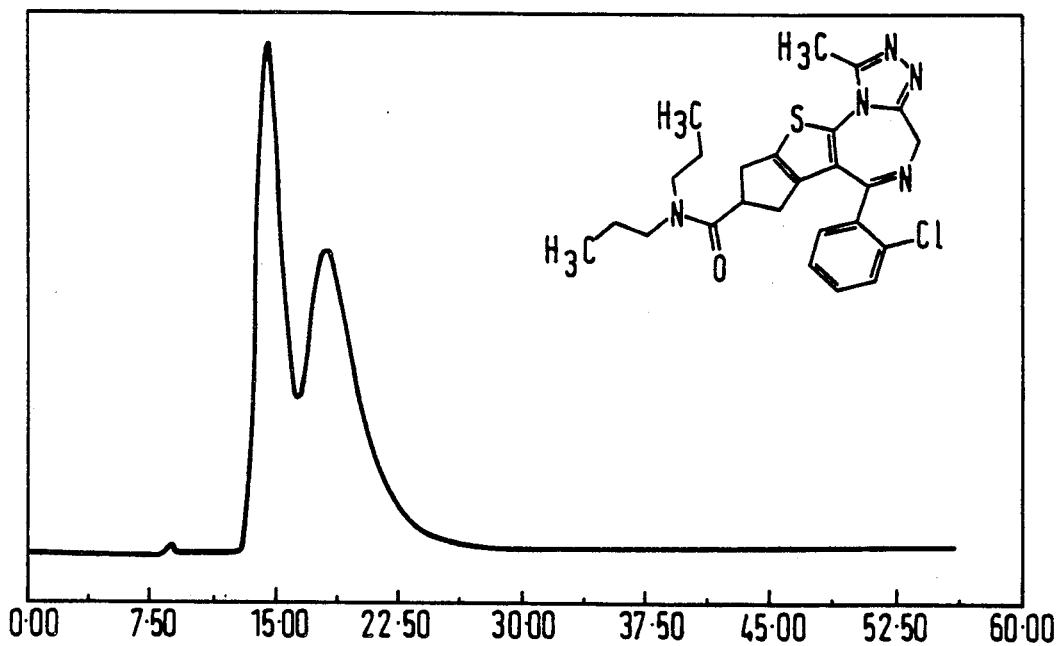
Figure 3:
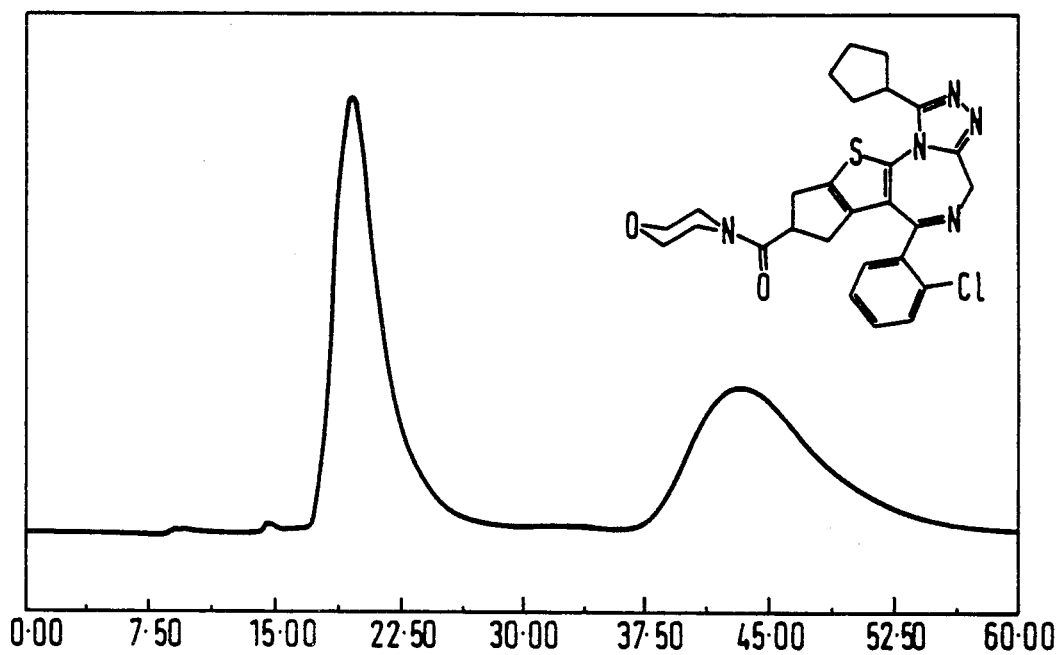
Figure 4:
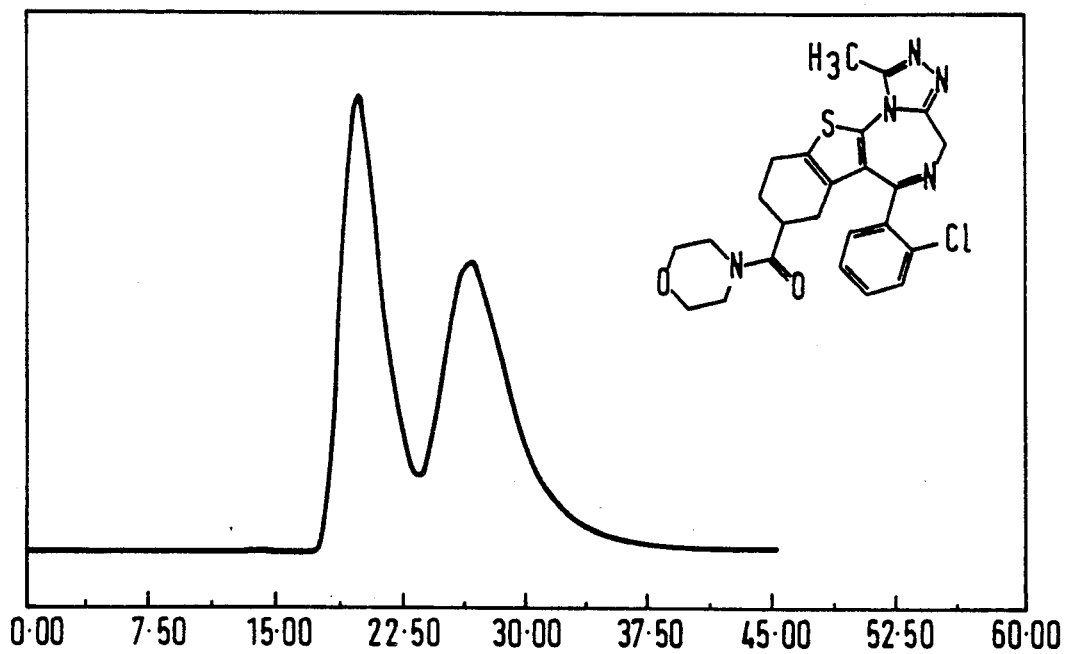
Figure 5:
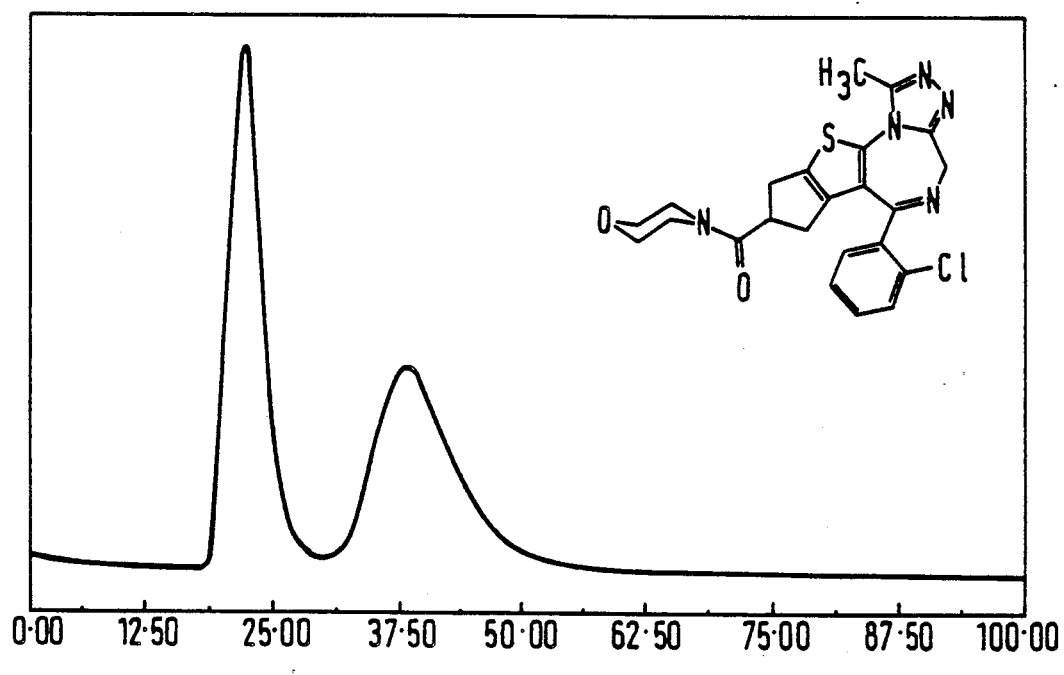

Of particular interest are the enantiomerically pure hetrazepines of general formula

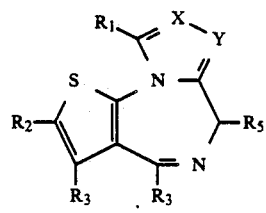

wherein $R_1$ represents hydrogen, a straight-chained or branched $C_{1-4}$-alkyl group, preferably methyl, which may optionally be substituted by hydroxy or halogen, a cyclopropyl group, a cyclobutyl group, a cyclopentyl group, a cyclohexyl group, or halogen, preferably chlorine or bromine;

$R_2$ represents a group of the formula

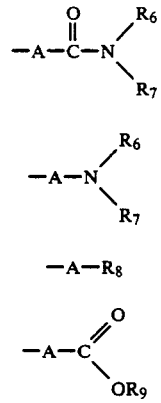

wherein A represents a branched or unbranched alkyl group having n carbon atoms, wherein n represents one of the numbers 0, 1, 2, 3, 4, 5, 6, 7 or 8, $R_6$ and $R_7$, which may be identical or different, represent hydrogen, phenyl, substituted phenyl, an optionally substituted $C_{3-6}$-cycloalkyl group, a branched or unbranched alkyl, alkenyl or alkynyl group having 1 to 10, preferably 1 to 4, carbon atoms, which may optionally be substituted by halogen, hydroxy, nitro, phenyl, substituted phenyl, amino, substituted amino, $C_{1-8}$, preferably $C_{1-4}$-alkoxy;

$R_6$ or $R_7$ represents a saturated or unsaturated five, six or seven-membered heterocyclic ring bound via a carbon or nitrogen atom and optionally mono- or polysubstituted by branched or unbranched $C_{1-4}$-alkyl; or $R_6$ and $R_7$ together with the nitrogen atom represent a saturated or unsaturated 5-, 6- or 7-membered ring which is optionally mono- or polysubstituted by branched or unbranched $C_{1-4}$-alkyl groups and which may contain as further heteroatoms nitrogen, oxygen or sulphur, whilst each additional nitrogen atom may be substituted by a branched or unbranched $C_{1-4}$-alkyl group, preferably methyl;

$R_8$ represents phenyl or substituted phenyl;

$R_9$ represents hydrogen or $C_{1-4}$-alkyl;

$R_3$ represents hydrogen or $C_{1-4}$-alkyl;

$R_4$ represents phenyl, wherein the phenyl ring may be mono- or polysubstituted, preferably by halogen, nitro and/or trifluoromethyl;

$R_5$ represents hydroxy or $C_{1-4}$-alkyl, optionally substituted by hydroxy or halogen or $R_2$ and $R_3$ together form a condensed five- or six-membered ring of formula

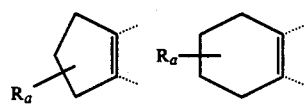

wherein $R_a$ represents a group of the formula

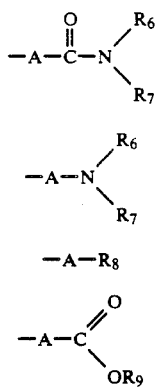

wherein A, $R_6$, $R_7$, $R_8$ and $R_9$ are defined as hereinbefore and $R_5$ represents hydrogen, hydroxy or $C_{1-4}$-alkyl, optionally substituted by hydroxy or halogen, and X and Y may both represent nitrogen or X may represent CH and Y represents nitrogen.

The preferred compounds of general formula 1 are those wherein
$R_1$ = methyl
$R_2$ = —$CH_2$—$CH_2$—$CONR_6R_7$
$R_2$ = —$CH_2$—$C_2$—$NR_6R_7$

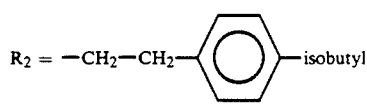

$R_3$ = hydrogen, $R_5$ = methyl
$R_2$ and $R_3$ together represent

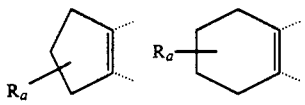

wherein
$R_a$ = $CONR_6R_7$
$R_5$ = hydrogen or methyl
$R_4$ = orthochlorophenyl
$R_6R_7$ are preferably $C_3H_7$ or together with the nitrogen form a morpholino group.

Compounds of general formula I wherein $R_2$ and $R_3$ form a condensed 5- or 6-membered ring and $R_5$ does not represent hydrogen contain two optically active carbon atoms in the ring system and constitute mixtures of diastereomers. These may be separated into their diastereomers by conventional methods, e.g. by separation by column chromatography on $SiO_2$ as the stationary phase and ethyl acetate/methanol as the mobile phase. The process according to the invention can then be used to separate the diastereomers into their enantiomers.

Examples of alkyl groups (including those which form part of other groups) include: methyl, ethyl, propyl, isopropyl, butyl, isobutyl, sec.-butyl, tert.-butyl, pentyl, isopentyl, hexyl, heptyl, octyl, nonyl and decanyl.

Examples of alkenyl groups are the alkyl groups mentioned above, provided that they have at least one double bond, such as for example vinyl (provided that no unstable enamines are formed), propenyl, isopropenyl, butenyl, pentenyl and hexenyl. Examples of alkynyl groups include the above-mentioned alkyl groups provided that they have at least one triple bond, such as propargyl, butynyl, pentynyl and hexynyl. Examples of cycloalkyl groups having 3 to 6 carbon atoms include cyclopropyl, cyclobutyl, cyclopentyl and cyclohexyl, which may be substituted by branched or unbranched $C_{1-4}$-alkyl, hydroxy and/or halogen.

Examples of substituted phenyl include: 3-chlorophenyl, 4-chlorophenyl, 3-bromophenyl, 4-bromophenyl, 4-fluoromethyl, 2-chlorophenyl, 2-bromophenyl, 3-fluorophenyl, 2,3-dichlorophenyl, 2-methylphenyl, 4-methylphenyl, 3-ethylphenyl, 4-propylphenyl, 4-isopropylphenyl, 4-butylphenyl, 4-tert.-butylphenyl, 4-isobutylphenyl, 4-pentylphenyl, 2,4-dimethylphenyl, 2-trifluoromethylphenyl, 3-trifluoro-methylphenyl, 4-trifluoromethylphenyl, 2-methoxyphenyl, 4-methoxyphenyl, 3-ethoxyphenyl, 2-propoxyphenyl, 4-butoxyphenyl, 2,4-dimethoxyphenyl, 3,4,5-trimethoxy-phenyl, 2-chlorobenzyl, 2,3-dichlorobenzyl, 2-methylbenzyl, 2-trifluoromethylbenzyl, 4-methoxybenzyl, 3,4,5-trimethoxybenzyl, 2-(2-chlorophenyl)ethyl.

Examples of optionally substituted, saturated or unsaturated heterocyclic 5-, 6- or 7-membered rings or heteroalkyl groups include: pyrrole, pyrroline, pyrrolidine, 2-methylpyrrolidine, 3-methylpyrrolidine, piperidine - optionally mono- or polysubstituted by $C_{1-4}$-alkyl - piperazine, N-methylpiperazine, N-ethyl-piperazine, N,N-propylpiperazine, N-benzylpiperazine, morpholine, thiomorpholine, imidazole, imidazoline, imidazolidine, triazole, pyrazole, pyrazoline, pyrazolidine, triazine, 1, 2, 3, 4 - tetrazine, 1, 2, 3, 5 - tetrazine, 1, 2, 4, 5 -tetrazine, whilst the above-mentioned heterocyclic groups may be substituted by $C_{1-4}$-alkyl, preferably methyl.

Examples of heterocyclic groups which may be linked via a carbon atom include for example thiophene, 2-methylthiophene, furan, tetrahydrofuran, 2-methyltetrahydrofuran, 2-hydroxymethylfuran, α-pyran, γ-pyran, 1,3-dioxolan, 1,2-oxathiolan, 1,2-oxathiepan, tetrahydropyran, thiolan, 1,3-dithian, 1,3-dithiolan, 1,3-dithiolene, wherein the heterocyclic group may be substituted by $C_{1-4}$-alkyl, $C_{1-4}$-alkoxy or halogen.

The term heterocyclic group within the scope of the above definitions generally denotes a 5- or 6-membered ring which may contain as heteroatoms oxygen, sulphur and/or nitrogen, such as for example thienyl, furyl, pyridyl, pyrimidyl, pyrazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl and indolyl.

According to the invention, racemates of general formula I can be separated into their enantiomers by a process of liquid chromatography using cellulose triacetate as the stationary phase. A suitable cellulose triacetate can be obtained for example from Merck of D-6100 Darmstadt under number 16 363.0250.

The mobile phase may consist of polar solvents or mixtures of solvents such as methanol, ethanol, methanol-water, ethanol-water, ethanol-hexane, ethanol-/isopropanol/hexane, the preferred solvent being methanol.

The preferred method of chromatography is high pressure liquid chromatography (HPLC), but low pressure and medium pressure chromatography are also suitable, albeit more time-consuming. By contrast with the prior art (EP 254 245) which describes separation only in analytical quantities, the process according to the invention can be used for separation on an industrial scale.

The Examples which follow are intended to illustrate the invention without restricting its scope.

EXAMPLE 1

80 g of (R,S) 6-(2-chlorophenyl)-8,9-dihydro-1-methyl-8-[(4-morpholinyl)carbonyl]-4H,7H-cyclopenta-[4,5]thieno[3,2-f][1,2,4]triazolo[4,3-a][1,4]diazepine (WEB 2170) are dissolved in 80 ml of methanol in an ultrasound bath. The solution is placed on a cellulose triacetate column (particle diameter 25-40 μm, measuring 500 mm × 200 mm in diameter). At a flow rate of 150 ml/min of pure methanol, the WEB 2170 is conveyed through the column and separated into its enantiomers. A throughflow polarimeter detector is used for detection. After working up in the usual way, 25 g (% of theory) of the (−)-isomer, rotational value $\alpha_D^{20} = -12.00$, from the first-running eluate.

From the second eluate, 20 g (% of theory) of the (+)-isomer, rotational value $\alpha_D^{20} = +9.50$, are isolated.

The following compounds are separated into their enantiomers analogously to Example 1.

EXAMPLE 2

(R,S)-6-(2-Chlorophenyl)-8,9-dihydro-8-(N,N-dipropylaminocarbonyl)-1-methyl-4H,7H-cyclopenta[4,5]-thieno[3,2-f][1,2,4]triazolo[4,3-a][1,4]diazepine

EXAMPLE 3

(R,S)-6-(2-Chlorophenyl)-1-cyclopentyl-8,9-dihydro-8-(morpholinocarbonyl)-4H,7H-cyclopenta[4,5]-thieno[3,2-f]-[1,2,4]triazolo[4,3-a][1,4]diazepine

EXAMPLE 4

(R,S)-6-(2-Chlorophenyl)-8,9-dihydro-1-methyl-8-(morpholinocarbonyl)-4H,7H-cyclohexa[4,5]-thieno[3,2-f]-[1,2,4]triazolo[4,3-a][1,4]diazepine

EXAMPLE 5

(R,S))-6-(2-Chlorophenyl)-8,9-dihydro-1-methyl-8-(morpholinocarbonyl)-4,7-cyclopenta[4,5]thieno[3,2-f]-[1,4]imidazolo[4,3-a][1,4]diazepine

What is claimed is:

1. In a method for separating enantiomers of a compound of the formula:

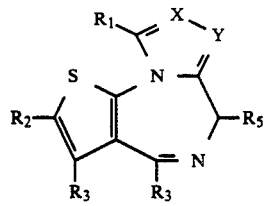

wherein
$R_1$ represents hydrogen, a straight-chained or branched $C_{1-4}$-alkyl group which may optionally be substituted by hydroxy or halogen, a cyclopropyl group, a cyclobutyl group, a cyclopentyl group, a cyclohexyl group, or halogen;
$R_2$ represents a group of the formula

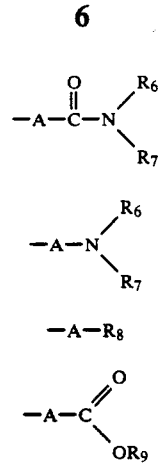

wherein A represents a branched or unbranched alkyl group having n carbon atoms, wherein n represents one of the numbers 0, 1, 2, 3, 4, 5, 6, 7 or 8, $R_6$ and $R_7$, which may be identical or different, represent hydrogen, phenyl, substituted phenyl, an optionally substituted $C_{3-6}$-cycloalkyl group, a branched or unbranched alkyl, alkenyl or alkynyl group having 1 to 10 carbon atoms, which may optionally be substituted by halogen, hydroxy, nitro, phenyl, substituted phenyl, amino, substituted amino, or $C_{1-8}$ alkoxy; or $R_6$ or $R_7$ represents a saturated or unsaturated five, six or seven-membered heterocyclic ring bound via a carbon or nitrogen atom and optionally mono- or polysubstituted by branched or unbranched $C_{1-4}$-alkyl; or $R_6$ and $R_7$ together with the nitrogen atom represent a saturated or unsaturated 5-, 6- or 7-membered ring which is optionally mono- or polysubstituted by branched or unbranched $C_{1-4}$-alkyl groups and which may contain as further heteroatoms nitrogen, oxygen or sulphur, wherein each additional nitrogen atom may be substituted by a branched or unbranched $C_{1-4}$-alkyl group;

$R_8$ represents phenyl or substituted phenyl;
$R_9$ represents hydrogen or $C_{1-4}$-alkyl;
$R_3$ represents hydrogen or $C_{1-4}$-alkyl;
$R_4$ represents phenyl, wherein the phenyl ring may be mono- or polysubstituted;
$R_5$ represents hydroxy or $C_{1-4}$-alkyl, optionally substituted by hydroxy or halogen; or
$R_2$ and $R_3$ together form a condensed five- or six-membered ring of formula

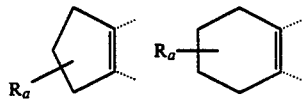

wherein $R_8$ represents a group of the formula

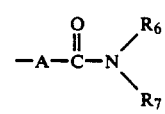

-continued

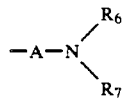

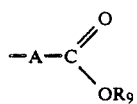

wherein A, R$_6$, R$_7$, R$_8$ and R$_9$ are defined as hereinbefore and R$_5$ represents hydrogen, hydroxy or C$_{1-4}$-alkyl, optionally substituted by hydroxy or halogen; and X and Y both represent nitrogen or X represents CH and Y represents nitrogen, by liquid chromatography comprising a stationary phase and a mobile phase, the improvement comprising using Cellulose triacetate as the stationary phase and a polar solvent, alone or in combination with other solvents, as the mobile phase.

2. A method, as recited in claim 1 wherein the mobile phase is selected from the group consisting of methanol, ethanol, methanol/water, ethanol/water, ethanol/hexane, and ethanol/isopropanol/hexane.

3. A method as recited in claim 1 wherein the liquid chromatography is high pressure liquid chromatography.

4. A method as recited in claim 1 wherein the compound is (R,S)6-(2-chloro-phenyl)-8,9-dihydro-1-methyl-8-[(4-morpholinyl)carbonyl]-4H,7H-cyclopenta-[4,5]thieno[3,2-f][1,2,4]triazolo[4,3-a][1,4]-diazepine.

* * * * *